US008816101B2

(12) United States Patent
Boustie et al.

(10) Patent No.: US 8,816,101 B2
(45) Date of Patent: Aug. 26, 2014

(54) PARACONIC ACIDS AS PIGMENTATION ACTIVATORS

(75) Inventors: Joel Boustie, Montgermont (FR); Marie-Dominique Galibert-Anne, Rennes (FR); Francoise Lohezic-le-Devehat, Orgeres (FR); Marylene Chollet-Krugler, La Chapelle Chaussee (FR); Sophie Tomasi, Rennes (FR)

(73) Assignees: Centre National de la Recherche Scientifique—CNRS, Paris Cedex (FR); Universite de Rennes 1, Rennes (FR); Centre Hospitalier Universitaire Pontchaillou, Rennes (FR)

( * ) Notice: Subject to any disclaimer, the term of this patent is extended or adjusted under 35 U.S.C. 154(b) by 0 days.

(21) Appl. No.: 13/582,935

(22) PCT Filed: Mar. 4, 2011

(86) PCT No.: PCT/FR2011/050454
§ 371 (c)(1),
(2), (4) Date: Sep. 5, 2012

(87) PCT Pub. No.: WO2011/107720
PCT Pub. Date: Sep. 9, 2011

(65) Prior Publication Data

US 2012/0329868 A1 Dec. 27, 2012

(30) Foreign Application Priority Data

Mar. 5, 2010 (FR) ..................................... 10 51622

(51) Int. Cl.
*C07D 307/00* (2006.01)

(52) U.S. Cl.
USPC .......................................... 549/323; 549/322

(58) Field of Classification Search
USPC ................................................. 549/322, 323
See application file for complete search history.

(56) References Cited

FOREIGN PATENT DOCUMENTS

WO 2004/006835 1/2004

OTHER PUBLICATIONS

Cavaltto et al. J Am Chem Soc. 70(11), 3724-3726, 1948.*
Bloomer et al. J. Chem. Soc. (C). 1970, 1848-1850.*
Abrahams et al. Planta Medica, vol. 74, issue 09, Jul. 2008.*
Cavallito et al., "Lactone aliphatic acids as antibacterial agents," J. Am. Chem. Soc., 70(11):3724-3726 (1948) XP002602594.
International Search Report in PCT/FR2011/050454 dated Jun. 29, 2011.
Liberge, "Synthese de molecules nouvelles a potentialites therapeutiques dans le traitement des troubles du metabolism (diabete, obesite, prise alimentaire) et du cancer," [Online] Universite des Sciences et Technologies de Lille—These, pp. 1-67, 151-155 (2004) XP002602595.
Muller, "Pharmaceutically relevant metabolites from lichens," Appl. Microbiol. Biotechnol., 56(1-2):9-16 (2001) XP002602593.

* cited by examiner

*Primary Examiner* — Nizal Chandrakumar
(74) *Attorney, Agent, or Firm* — McAndrews, Held & Malloy Ltd.

(57) ABSTRACT

The invention relates to a mixture comprising protolichesterinic acid or a salt thereof or a diastereoisomer thereof or a derivative thereof, and lichesterinic acid or a salt thereof or an enantiomer thereof or a derivative thereof, for use for stimulating pigmentation of the skin and/or of its appendages. The invention also relates to derivatives of lichesterinic acid of formula (A).

5 Claims, 2 Drawing Sheets

PARACONIC ACIDS AS PIGMENTATION ACTIVATORS

The present application is filed pursuant to 35 U.S.C. 371 as a U.S. National Phase application of International Patent Application No. PCT/FR2011/050454, which was filed Mar. 4, 2011, claiming the benefit of priority to French Patent Application No. 1051622, which was filed on Mar. 5, 2010. The aforementioned applications are incorporated herein by reference in their entireties.

The invention relates to a mixture comprising protolichesterinic acid or a salt thereof or a diastereoisomer thereof or a derivative thereof, and lichesterinic acid or a salt thereof or an enantiomer thereof or a derivative thereof, to be used for stimulating pigmentation of the skin and/or of its appendages.

The invention also relates to compounds of formula (A), and use thereof for stimulating pigmentation of the skin and/or of its appendages.

The colour of human skin and its appendages (hair, nails, body hair etc.) depends on various factors and notably on the seasons of the year, race, sex and age. It is mainly determined by the concentration of melanin produced by the melanocytes. The melanocytes are specialized cells which, through the action of particular organelles, the melanosomes, synthesize melanin.

It is known that in most populations, brown coloration of the skin or maintaining a constant coloration of the hair are important aspirations. Moreover, there are pigmentation disorders, for example vitiligo, which is an auto-immune disease characterized by the appearance of white patches on the skin associated with a defect of pigmentation.

There is therefore a real need for a product that facilitates and/or improves the pigmentation of the skin and/or of its appendages.

In this respect, numerous solutions have been offered in the area of artificial coloration. In fact, exogenous dyes have been synthesized and are felt to give the skin and/or the hair a coloration that is as close as possible to a natural coloration.

Excellent results have certainly been obtained by the solutions proposed in the prior art, but even so, stimulation of the pigmentation of the skin or of its appendages by the natural route (melanogenesis) is still the ideal means of pigmentation. The discovery of substances having an effect on the pigmentation of the skin or of its appendages is still a major objective of research in this area.

Surprisingly, the inventors have now discovered that certain compounds derived from lichen stimulate the natural pathway of melanogenesis and therefore promote pigmentation of the skin or of its appendages.

Thus, the invention relates to a mixture comprising (i) protolichesterinic acid or a salt thereof or a diastereoisomer thereof or a derivative thereof, and (ii) lichesterinic acid or a salt thereof or an enantiomer thereof or a derivative thereof ("mixture" hereinafter), the weight ratio (i):(ii) being between 1:4 and 4:1, for use as a medicinal product.

In particular, the invention relates to a mixture comprising (i) protolichesterinic acid or a salt thereof or a diastereoisomer thereof or a derivative thereof, and (ii) lichesterinic acid or a salt thereof or an enantiomer thereof or a derivative thereof ("mixture" hereinafter), the weight ratio (i):(ii) being between 1:4 and 4:1, for use for stimulating pigmentation of the skin and/or of its appendages. Preferably, the mixture in the weight ratio indicated is used for treating hypopigmentation disorders.

The invention also relates to the use of said mixture for preparing a medicinal product for stimulating pigmentation of the skin and/or of its appendages, preferably for treating hypopigmentation disorders.

The mixture according to the invention can further comprise dihydrolichesterinic acid, notably roccellaric acid.

Figure 1:
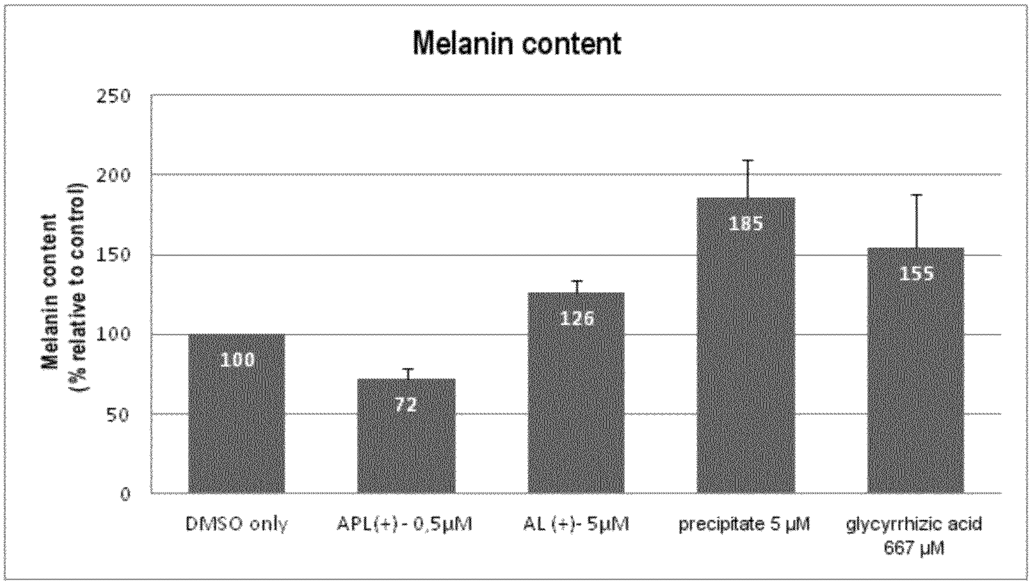
FIG. 1 shows the melanin content of B16 cells treated for 72 hours in the presence of test substances.

"Appendages" notably means the hair, body hair and nails.

In the present application, "protolichesterinic acid" means (+)-protolichesterinic acid, and "lichesterinic acid" means (+)-lichesterinic acid.

(+)-Protolichesterinic acid and (+)-lichesterinic acid are paraconic acids (i.e. possessing an α-methylene-γ-lactone ring β-substituted with an acid function) of the following respective formulae (I) and (II):

(I)

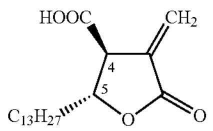

(II)

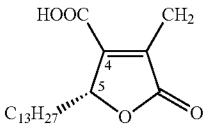

These compounds are extracts of lichens, and notably of the lichen *Cetraria islandica* Ach. or Iceland lichen.

(+)-Protolichesterinic acid (formula (I)) is of 4S,5R configuration owing to the two asymmetric carbons in positions 4 and 5 of the ring.

(+)-Lichesterinic acid (formula (II)) is of 5R configuration owing to the asymmetric carbon in position 5 of the ring; the double bond is of the endo type.

"Salts" of protolichesterinic acid or of lichesterinic acid means the salts of these compounds with alkali metals such as sodium, potassium or lithium, but also salts of these compounds with ammonium ions.

"Diastereoisomers" of protolichesterinic acid notably means the 4R,5S diastereoisomer of protolichesterinic acid. "Enantiomer" of lichesterinic acid means the 5S enantiomeric derivative of lichesterinic acid.

"Derivatives" of protolichesterinic acid or of lichesterinic acid means the esters of these compounds with methanol or ethanol, but also the compounds of the following formula (A), the salts thereof and the enantiomers thereof:

(A)

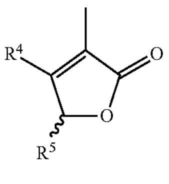

in which $R^4$ represents a hydrogen atom, an alkyl radical having from 1 to 6 carbon atoms, an unsubstituted phenyl radical (Ph), an unsubstituted phenethyl radical ($PhCH_2CH_2$) or the group COOR where R=Na, K, Li, $NH_4$, H, methyl or ethyl, and $R^5$ is selected from a hydrogen atom, a linear or branched $C_1$ to $C_{13}$ alkyl radical, $CH_2CCH$, Ph, $PhCH_2$, $PhCH_2CH_2$ and $(CH_2)_{13}COR^6$ where $R^6$=$OCH_3$, OH or $CH_3$, with the proviso that when $R^4$ represents COOH, $R^5$ is different from the linear alkyl radical $C_{13}H_{27}$.

In the present invention, unless stated otherwise, "alkyl radical having from 1 to 6 carbon atoms" means the methyl, ethyl, isopropyl, n-propyl, n-butyl, t-butyl and i-butyl radicals. Preferably, the alkyl radical having from 1 to 6 carbon atoms is an n-butyl radical.

"Linear or branched $C_1$ to $C_{13}$ alkyl radical" means a linear or branched alkyl radical having from 1 to 13 carbon atoms, such as notably the pentyl, nonyl or tridecyl radicals.

The mixture according to the invention is used for stimulating pigmentation of the skin and/or of its appendages. Preferably, the mixture according to the invention is used for treating hypopigmentation disorders.

"Hypopigmentation disorders" preferably means vitiligo, genetic hypopigmentation diseases, pityriasis versicolor, post-inflammatory hypopigmentations, hypopigmentations or depigmentations due to skin grafts, photo-induced hypopigmentations or depigmentations, post-healing hypopigmentations or depigmentations, hypopigmentations or depigmentations due to ageing, and depigmentation of the hair.

Vitiligo is characterized by the appearance of white patches on the skin. There are two main forms: the "generalized" form is characterized by patches that are roughly symmetric relative to the median axis of the body and represents almost nine tenths of cases. The segmental form is a little more common in children, especially on the face, with quicker progression. In the later stages, depigmentation of body hair or of the hair may be seen. This disease does not cause physical pain but may be upsetting in aesthetic terms.

"Genetic hypopigmentation diseases" notably denotes albinism, piebaldism (characterized by a white forelock) or xeroderma pigmentosum.

Albinism is a genetic disease characterized by an absence of pigmentation of the skin, body hair, hair, and eyes, due to absence of melanin. This disease is known in several possible forms: partial albinism (ocular albinism) or total albinism (oculocutaneous albinism). Albinos have defective vision and are susceptible to skin cancers if they are not protected from the sun.

Piebaldism is a rare autosomal dominant disease. It is characterized by triangular or diamond-shaped frontal achromia with a white forelock.

Xeroderma pigmentosum, the so-called "moon children disease", is a rare autosomal genetic disease that affects about 3000 to 4000 persons throughout the world. This epitheliomatous pigmentary disease, which develops during childhood, increases the risk of multiple skin cancers by a factor of 1000. Children with this disease are extremely sensitive to sunlight and can only survive if extreme precautions are taken.

Pityriasis versicolor is a common benign disorder caused by the excessive proliferation of a fungus belonging to the group of yeasts of the genus *Malassezia*. The yeasts of the genus *Malassezia* are present on the surface of normal human skin and can, in certain patients, cause pityriasis versicolor, which is reflected in pigmented or depigmented patches on the trunk.

Post-inflammatory hypopigmentations follow certain inflammatory disorders (in particular bullous dermatoses), burns and skin infections, and appear on scars and areas of atrophic skin. Although the pigmentation is diminished, the skin is not necessarily ivory white and may eventually repigment spontaneously.

Preferably, the hypopigmentation disorder is vitiligo.

The mixture according to the invention comprises (i) protolichesterinic acid or a salt thereof or a diastereoisomer thereof or a derivative thereof, and (ii) lichesterinic acid or a salt thereof or an enantiomer thereof or a derivative thereof, in a respective weight ratio (i):(ii) between 1:4 and 4:1, preferably between 2:3 and 3:1, more preferably between 1:1 and 5:2.

Preferably, the mixture according to the invention comprises from 20 to 80 wt %, relative to the total weight of the mixture, of protolichesterinic acid or a salt thereof or a diastereoisomer thereof or a derivative thereof, preferably from 40 to 60 wt %.

Preferably, the mixture according to the invention comprises from 20 to 80 wt %, relative to the total weight of the mixture, of lichesterinic acid or a salt thereof or an enantiomer thereof or a derivative thereof, preferably from 40 to 60 wt %.

The specific weight ratios of protolichesterinic acid, a salt thereof, diastereoisomer thereof or derivative thereof, and of lichesterinic acid, a salt thereof, enantiomer thereof or derivative thereof, as described above, have a synergistic effect stimulating the pigmentation of the skin and/or of its appendages, as demonstrated in example 1.

"Synergistic effect" or "synergy" means that the mixture of protolichesterinic acid, a salt thereof, diastereoisomer thereof or derivative thereof and of lichesterinic acid, a salt thereof, enantiomer thereof or derivative thereof according to the invention, has a pigmenting activity greater than the sum of the pigmenting activity of each compound used separately.

Preferably, the mixture according to the invention comprises protolichesterinic acid and lichesterinic acid.

When the mixture comprises dihydrolichesterinic acid, it comprises this acid in an amount between 1 and 15 wt % relative to the total weight of the mixture, preferably between 3 and 10 wt %, preferably between 3 and 7 wt % relative to the total weight of the mixture.

Preferably, the mixture according to the invention comprises protolichesterinic acid, lichesterinic acid and dihydrolichesterinic acid.

Preferably, the mixture according to the invention consists of from 50 to 70% of protolichesterinic acid, from 20 to 40% of lichesterinic acid, and from 3 to 10% of dihydrolichesterinic acid, the percentages being expressed by weight relative to the total weight of the mixture.

The mixture according to the invention can be administered in a composition orally, systemically or topically by application on the skin and/or its appendages. The composition comprising the mixture according to the invention can be in all pharmaceutical forms, depending on the method of administration.

Preferably, the mixture according to the invention is included in a composition that is administered topically on the skin and/or its appendages.

Protolichesterinic acid, a salt thereof, diastereoisomer thereof or derivative thereof according to the invention, and lichesterinic acid, a salt thereof, enantiomer thereof or derivative thereof according to the invention can be packaged together in one and the same composition, or else separately in the form of a kit, the components of which will be mixed extemporaneously.

For the oral route, the compositions can be in the form of tablets, capsules, sugar-coated pills, syrups, suspensions, solutions, powders, granules, emulsions, microspheres or nanospheres or lipid or polymeric vesicles permitting controlled release.

For topical application on the skin, the composition can notably be in the form of aqueous or oily solution or in the form of dispersion of the lotion or serum type; emulsion of liquid or semi-liquid consistency of the milk type, obtained by dispersion of an oily phase in an aqueous phase (O/W) or inverted (W/O); emulsion of soft consistency of the cream type; aqueous or anhydrous gel; or microcapsules or microparticles, or vesicular dispersions of the ionic and/or non-ionic type. These compositions are prepared by usual methods known by a person skilled in the art.

For topical application on the hair, the composition can be in the form of aqueous, alcoholic or aqueous-alcoholic solutions; gels; emulsions; mousses; or in the form of compositions for aerosols also comprising a propellant under pressure. The composition according to the invention can also be a hair care composition, and notably a shampoo, a treatment lotion, a cream or a styling gel, or a lotion or a gel against hair loss.

For systemic application, the composition can be in the form of aqueous or oily solution or in the form of serum.

The composition comprising the mixture according to the invention can notably comprise a fatty phase, an emulsifier, a solvent, a penetration promoter or a gelling agent (lipophilic or hydrophilic).

When the composition comprises a fatty phase, the latter comprises at least one oil or a wax.

As oils or waxes usable in the invention, we may mention mineral oils (liquid paraffin), vegetable oils (liquid fraction of shea butter, sunflower oil), animal oils (perhydrosqualene), synthetic oils (purcelline oil), silicone oils or waxes (cyclomethicone), fluorinated oils (perfluoropolyethers), beeswax, carnauba wax or paraffin wax, as well as fatty alcohols and fatty acids (stearic acid).

The composition can also comprise at least one emulsifier. This emulsifier can be anionic, cationic, non-ionic or amphoteric.

As solvents usable according to the invention, we may mention lower alcohols, notably ethanol and isopropanol, and propylene glycols.

As penetration promoters usable according to the invention, we may mention glycols, notably 1,2-propanediol (or propylene glycol) and polyethylene glycols.

As hydrophilic gelling agents usable in the invention, we may mention carboxyvinyl polymers (carbomer), acrylic copolymers such as acrylate/alkyl acrylate copolymers, polyacrylamides, polysaccharides such as hydroxypropylcellulose, natural gums and clays, and, as lipophilic gelling agents, we may mention modified clays such as bentones, metal salts of fatty acids such as aluminium stearates and hydrophobic silica, ethylcellulose, polyethylene.

According to the invention, the composition can combine the mixture with other active agents.

Among these active agents, we may mention as examples:

self-tanning agents such as dihydroxyacetone (DHA) or erythrulose;

agents improving hair restoring activity and/or activity for stopping hair loss, which have already been described for said activity, for example minoxidil, aminexil, esters of nicotinic acid, notably including tocopherol nicotinate, benzyl nicotinate and nicotinates of $C_1$-$C_6$ alkyls such as methyl or hexyl nicotinates;

steroidal anti-inflammatory agents, such as hydrocortisone, betamethasone valerate or clobetasol propionate, or non-steroidal anti-inflammatory agents for example ibuprofen and salts thereof, diclofenac and salts thereof, acetylsalicylic acid, acetaminophen (paracetamol) or glycyrrhizic acid;

antifungal agents such as ketoconazole, selenium sulphide, itraconazole or fluconazole;

antipruritics such as thenalidine, trimeprazine or cyproheptadine.

The composition can also comprise conventional additives, such as preservatives, antioxidants, perfumes, fillers, odour absorbers and colorants.

The amounts of these various additives are those used conventionally, for example from 0.01 to 20 wt % relative to the total weight of the composition.

In addition to the above mixture and the applications thereof, the invention also relates to a compound of formula (A), a salt thereof or an enantiomer thereof:

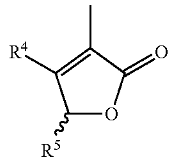

(A)

in which $R^4$ represents a hydrogen atom, an alkyl radical having from 1 to 6 carbon atoms, an unsubstituted phenyl radical, an unsubstituted phenethyl radical or a group COOR where R=Na, K, Li or $NH_4$, H, methyl or ethyl, with the proviso that:

when $R^4$ represents a hydrogen atom, $R^5$ is selected from a linear or branched $C_{10}$ or $C_{12}$ alkyl radical, $CH_2C{\equiv}CH$ and $(CH_2)_{13}COR^6$ where $R^6$=$OCH_3$, OH or $CH_3$;

when $R^4$ represents an alkyl radical having from 1 to 6 carbon atoms, preferably an n-butyl radical, $R^5$ is selected from a linear or branched $C_2$, $C_3$ or $C_5$ to $C_{13}$ alkyl radical, $CH_2CCH$, Ph, $PhCH_2CH_2$ and $(CH_2)_{13}COR^6$ where $R^6$=$OCH_3$, OH or $CH_3$;

when $R^4$ represents an unsubstituted phenethyl radical, $R^5$ is selected from H, a linear or branched $C_1$ to $C_{13}$ alkyl radical, $CH_2CCH$, Ph, $PhCH_2$, $PhCH_2CH_2$ and $(CH_2)_{13}COR^6$ where $R^6$=$OCH_3$, OH or $CH_3$;

when $R^4$ represents an unsubstituted phenyl radical, $R^5$ is selected from a linear or branched $C_3$ to $C_{13}$ alkyl radical, $CH_2CCH$, Ph, $PhCH_2$, $PhCH_2CH_2$ and $(CH_2)_{13}COR^6$ where $R^6$=$OCH_3$, OH or $CH_3$;

when $R^4$ represents COONa, $R^5$ is selected from H, a linear or branched $C_1$ to $C_{13}$ alkyl radical, $CH_2CCH$, Ph, $PhCH_2$, $PhCH_2CH_2$ and $(CH_2)_{13}COR^6$ where $R^6$=$OCH_3$, OH or $CH_3$;

when $R^4$ represents COOH, $R^5$ is selected from a linear or branched $C_2$ to $C_4$ or $C_6$, $C_7$, $C_9$, $C_{10}$ or $C_{12}$ alkyl radical, $CH_2CCH$, Ph, $PhCH_2$, $PhCH_2CH_2$ and $(CH_2)_{13}COR^6$ where $R^6$=$OCH_3$ or OH;

when $R^4$ represents $COOCH_3$, $R^5$ is selected from a linear or branched $C_2$ to $C_4$ or $C_6$ to $C_{12}$ alkyl radical, $CH_2CCH$, $PhCH_2$, $PhCH_2CH_2$ and $(CH_2)_{13}COR^6$ where $R^6$=$OCH_3$ or OH; and when $R^4$ represents $COOCH_2CH_3$, $R^5$ is selected from a linear or branched $C_2$ to $C_{13}$ alkyl radical, $CH_2CCH$, Ph, $PhCH_2$, $PhCH_2CH_2$ and $(CH_2)_{13}COR^6$ where $R^6$=$OCH_3$, OH or $CH_3$.

Said compounds can be incorporated in a pharmaceutical composition; thus, the invention relates to a pharmaceutical composition comprising at least one such compound, in a physiologically acceptable vehicle.

"Physiologically acceptable vehicle" means a vehicle compatible with the skin, mucosae and appendages.

Preferably, the compound of formula (A), a salt thereof or an enantiomer thereof has the following structure:

(A)

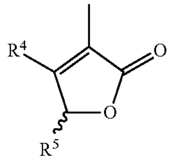

in which $R^4$ represents a hydrogen atom, an alkyl radical having from 1 to 6 carbon atoms, an unsubstituted phenyl radical, an unsubstituted phenethyl radical or a group COOR where R=Na, K, Li or $NH_4$, H, methyl or ethyl, with the proviso that:

when $R^4$ represents a hydrogen atom, $R^5$ is selected from a linear or branched $C_{10}$ or $C_{12}$ alkyl radical, $CH_2C{\equiv}CH$ and $(CH_2)_{13}COR^6$ where $R^6$=$OCH_3$, OH or $CH_3$;

when $R^4$ represents an alkyl radical having from 1 to 6 carbon atoms, preferably an n-butyl radical, $R^5$ is selected from a linear or branched $C_2$, $C_3$ or $C_5$ to $C_{13}$ alkyl radical, $CH_2CCH$, Ph, $PhCH_2CH_2$ and $(CH_2)_{13}COR^6$ where $R^6$=$OCH_3$, OH or $CH_3$;

when $R^4$ represents an unsubstituted phenethyl radical, $R^5$ is selected from H, a linear or branched $C_1$ to $C_{13}$ alkyl radical, $CH_2CCH$, Ph, $PhCH_2$, $PhCH_2CH_2$ and $(CH_2)_{13}COR^6$ where $R^6$=$OCH_3$, OH or $CH_3$;

when $R^4$ represents an unsubstituted phenyl radical, $R^5$ is selected from a linear or branched $C_3$ to $C_{13}$ alkyl radical, $CH_2CCH$, Ph, $PhCH_2$, $PhCH_2CH_2$ and $(CH_2)_{13}COR^6$ where $R^6$=$OCH_3$, OH or $CH_3$;

when $R^4$ represents COONa, $R^5$ is selected from H, a linear or branched $C_1$ to $C_{13}$ alkyl radical, $CH_2CCH$, Ph, $PhCH_2$, $PhCH_2CH_2$ and $(CH_2)_{13}COR^6$ where $R^6$=$OCH_3$, OH or $CH_3$;

when $R^4$ represents COOH, $R^5$ is selected from a linear or branched $C_2$ to $C_4$ or $C_6$, $C_7$, $C_9$, $C_{10}$ or $C_{12}$ alkyl radical, $CH_2CCH$, $PhCH_2$, $PhCH_2CH_2$ and $(CH_2)_{13}COR^6$ where $R^6$=$OCH_3$ or OH, preferably $R^5$ is selected from $CH_2CCH$ and $(CH_2)_{13}COR^6$ where $R^6$=$OCH_3$ or OH;

when $R^4$ represents $COOCH_3$, $R^5$ is selected from a linear or branched $C_2$ to $C_4$ or $C_6$ to $C_{12}$ alkyl radical, $CH_2CCH$, $PhCH_2$, $PhCH_2CH_2$ and $(CH_2)_{13}COR^6$ where $R^6$=$OCH_3$ or OH, preferably $R^5$ is selected from $CH_2CCH$ and $(CH_2)_{13}COR^6$ where $R^6$=$OCH_3$ or OH; and when $R^4$ represents $COOCH_2CH_3$, $R^5$ is selected from a linear or branched $C_2$ to $C_{13}$ alkyl radical, $CH_2CCH$, Ph, $PhCH_2$, $PhCH_2CH_2$ and $(CH_2)_{13}COR^6$ where $R^6$=$OCH_3$, OH or $CH_3$.

The invention also relates to a compound of formula (A), a salt thereof or an enantiomer thereof, in which $R^4$ represents a hydrogen atom, an alkyl radical having from 1 to 6 carbon atoms, notably an n-butyl radical, an unsubstituted phenyl radical, an unsubstituted phenethyl radical or the group COOR where R=Na, K, Li, $NH_4$, H, methyl or ethyl, and $R^5$ is selected from a hydrogen atom, a linear or branched $C_1$ to $C_{13}$ alkyl radical, $CH_2CCH$, Ph, $PhCH_2$, $PhCH_2CH_2$ and $(CH_2)_{13}COR^6$ where $R^6$=$OCH_3$, OH or $CH_3$, with the proviso that when $R^4$ represents COOH, $R^5$ is different from the linear alkyl radical $C_{13}H_{27}$, for use as a medicinal product. Preferably, said derivative is used for stimulating pigmentation of the skin and/or of its appendages.

Several methods will be envisaged depending on the nature of the radicals $R^4$ and $R^5$ of the compounds of formula (A). The method hereunder describes both the enantioselective synthesis of the compounds of formula (A), and the synthesis of the corresponding protolichesterinic derivative with $R^4$=COOR where R=Na, H, $CH_3$ or $C_2H_5$ and $R^5$=linear or branched $C_1$-$C_{13}$ alkyl radical:

It is an enantioselective synthesis in 8 steps, the first 6 of which (steps a-f) are described by S. Braukmüller and R. Brückner, *Eur. J. Org. Chem.* 2006, 2110-2118. Enantiocontrol is provided by steps b and d.

The condensation of methyl aldehyde on methyl hydrogenomalonate (step a) leads to a trans β,γ-unsaturated carboxylic ester. Sharpless asymmetric dihydroxylation gives an enantiopure β-hydroxy-γ-lactone (step b). After dehydration (step c) and selective trans-addition of tris(methylthio)methane (step d), the compound is converted to paraconic acid (step e). α-Activation in the presence of methyl magnesium carbonate followed by decarboxylative methylenation leads to the derivative of (+) or (−) protolichesterinic acid (step f). Esterification (step g) followed by isomerization of the double bond exo to endo in the presence of a catalytic amount of rhodium chloride leads to certain derivatives of formula (A) (step h).

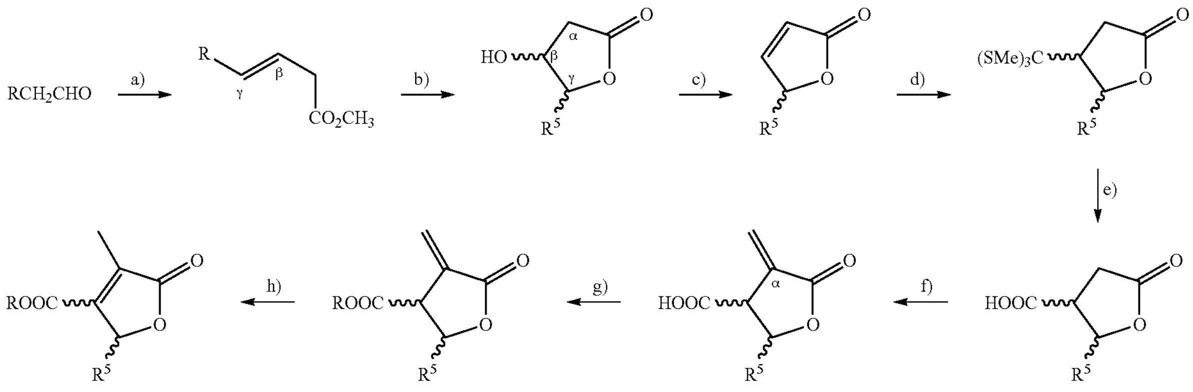

a) $HOOCCH_2CO_2C_2H_5$ (1.0 eq), $NEt_3$ (1.0 eq), 90° C., 3 h;

b) AD mix-α® or AD mix-β®, $MeSO_2NH_2$ (1.0 eq), t-BuOH/$H_2O$ (1:1), 0° C., 40 h;

c) MsCl (1.1 eq), $NEt_3$ (2.1 eq), $CH_2Cl_2$, 0° C., 15 min;

d) $HC(SMe)_3$ (1.1 eq), THF, −78° C., nBuLi (1.1 eq), 2-2.5 h; addition of furanone, 1.5-2 h;

e) HgO (5.0 eq), THF/$H_2O$ (4:1), $BF_3.OEt_2$ (15 eq), RT 2.5 h;
f) (i) MeOMg[O(C═O)Ome] (38 eq) in DMF, 135-140° C., 70 h, isolation of crude product; (ii) crude product, HOAc/NaOAc/formalin (=35-40% aq. solution of formaldehyde)/N-methylaniline (excess; 4:0.03:3:1), RT., 2 h;
g) $CH_3OH$ (1.0 eq) or $C_2H_5OH$ (1.0 eq), $H_2SO_4$ (1 eq), $CH_2Cl_2$, 18 h;
h) if R=H: $NEt_3$, DMF, 18 h, if R=$CH_3$, $C_2H_5$: $RhCl_3$, x $H_2O$ (0.1 eq), EtOH/$H_2O$ (10:1), 65° C., 18 h.

The invention also relates to the cosmetic use of a mixture comprising (i) protolichesterinic acid or a salt thereof or a diastereoisomer thereof or a derivative thereof, and (ii) lichesterinic acid or a salt thereof or an enantiomer thereof or a derivative thereof, in a weight ratio (i):(ii) between 1:4 and 4:1, as an agent for stimulating pigmentation of the skin and/or of its appendages.

The invention finally relates to the cosmetic use of a compound of formula (A) as an agent for stimulating pigmentation of the skin and/or of its appendages.

Of course, a person skilled in the art will take care not to introduce compounds in the composition used in the present invention in such a way that said compounds counteract the desired technical effect that is the object of the present invention.

Examples will now be given for purposes of illustration, which are not intended to limit the scope of the invention in any way.

EXAMPLE 1

Pigmenting Activity In Vitro of the Mixture of Protolichesterinic Acid (APL (+)) and Lichesterinic Acid (AL (+))

Protocol: The melanin content of B16 murine cells is determined by spectrophotometry.

The cells are seeded in 10-cm Petri dishes at a density of $1\times10^6$ per dish and are treated every 24 hours for 72 hours with the specified dose of purified lichenic substance, dissolved in DMSO. After dilution, the final concentration of DMSO does not exceed 0.1%, which corresponds to the control solution indicated as DMSO in FIG. 1. After treatment, the cells are washed twice with PBS and recovered by treatment with trypsin. The number of cells recovered is estimated by counting using a haemocytometer. One fraction is used for determining the melanin content and a second fraction for the concentration of protein. The melanin content is determined from the absorbance at 405 nm (VersaMax Microplate Reader, Molecular Devices, USA) of the cellular solution after solubilization of the melanin with 1M sodium hydroxide, for 15 min at 80° C. The protein concentration is determined according to the protocol of the "DC Protein Assay" kit developed by Bio-Rad Laboratories, USA. For each sample treated, the melanin content is referred to the amount of protein and expressed as percentage relative to the control situation (DMSO solution only). Each measurement is performed in triplicate and each experiment is carried out independently for a minimum of 3 times.

The results are presented in FIG. 1. FIG. 1 shows the melanin content of the B16 cells treated for 72 h in the presence of purified lichenic substances (APL (+) and AL(+)) or semi-purified (precipitate=APL/AL/roccellaric acid mixture, hereinafter ADL: 65/30/5 by weight, therefore weight ratio of 13:6:1) and of a positive control, glycyrrhizic acid.

The molecules tested, with their concentrations expressed in μM, are shown on the abscissa.

On the ordinate, the melanin content is expressed as percentage relative to the control (DMSO alone=concentration of 0.1%).

The results show that:

- protolichesterinic acid alone at 0.5 μM has a depigmenting effect (72% of pigmentation relative to the control, i.e. 28% of depigmentation);
- lichesterinic acid alone at 5 μM has a moderate pro-pigmenting effect (26% of pigmentation);
- the mixture of protolichesterinic acid and lichesterinic acid has a large pro-pigmenting effect (85% of pigmentation), which is opposite to that of protolichesterinic acid alone, and 3 to 4 times greater than that of lichesterinic acid alone.

The results obtained therefore demonstrate the synergistic activity of the mixture according to the invention.

EXAMPLE 2

Evaluation In Vitro of Tyrosinase Activity Induced by the Mixture of Protolichesterinic Acid and Lichesterinic Acid Protocol: The enzymatic activity of the endogenous enzyme tyrosinase is determined by measurement, at 450 nm, of the amount of substrate DOPA oxidized to DOPAchrome. As above, the cells are seeded in 10-cm Petri dishes at a density of $1\times10^6$ per dish and are treated every 24 hours for 72 hours with the specified dose of purified lichenic substance and solubilized in DMSO. After dilution, the final concentration of DMSO does not exceed 0.1%, which corresponds to the control solution, to which no product was added. After treatment, the cells are washed twice with PBS and recovered by treatment with trypsin. The number of cells recovered is estimated by counting using a haemocytometer. The cells are lysed by adding a solution of Triton X-100 (1% in PBS 1×). One milliliter of a solution of L-DOPA (1 ml at 10 mM), prepared extemporaneously, is added to each sample of cellular lysate (400 μl) and incubated in the dark at 37° C. with time kinetics from 30 min to 8 h. The amount of DOPAchrome formed is measured by spectrophotometry at 450 nm (Labsystems multiskan RC). The amount of DOPAchrome formed correlates with the enzymatic activity of the enzyme tyrosinase. Each measurement is performed in triplicate and each experiment is carried out independently for a minimum of 3 times.

Figure 2:
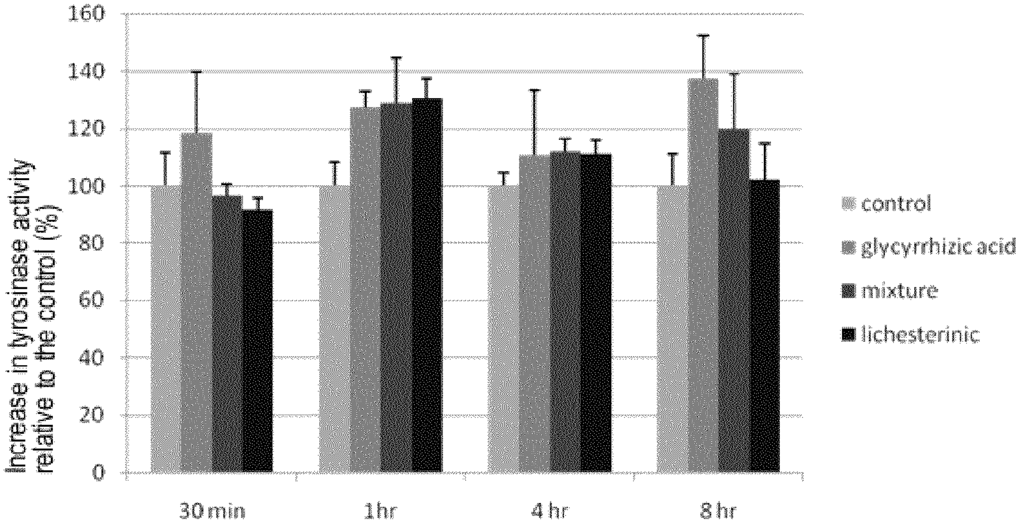
FIG. 2 shows tyrosinase activity over time in the presence of test substances.

The results are presented in FIG. 2. FIG. 2 corresponds to measurement of the enzymatic activity of the endogenous enzyme tyrosinase in the presence of lichesterinic acid, of the APL/AL/ADL mixture: 65/30/5—weight ratio of 13:6:1—(=mixture), glycyrrhizic acid (=positive control) and with the dilution solvent alone (=control).

The abscissa shows the contact time of the products before measurement of DOPAchrome formed for each of the tests.

On the ordinate, the percentage of DOPAchrome generated relative to the control (DMSO alone at 0.1%) reflects the enzymatic activity of the tyrosinase.

For each time (30 min, 1 h, 4 h and 8 h), the first histograms correspond to the control, the second correspond to glycyrrhizic acid, the third correspond to the APL/AL/ADL mixture (65/30/5), and the fourth correspond to lichesterinic acid alone.

EXAMPLE 3

Formulation According to the Invention

A mixture of protolichesterinic acid, lichesterinic acid and dihydrolichesterinic (or roccellaric) acid is prepared in respective proportions by weight of 13:6:1.

This mixture is incorporated in propylene glycol (or 1,2-propanediol) to a final concentration of 50 μM.

The invention claimed is:

1. A mixture comprising (i) protolichesterinic acid or a salt thereof or a diastereoisomer thereof, and (ii) lichesterinic acid or a salt thereof or an enantiomer thereof, in a weight ratio (i):(ii) between 2:3 and 3:1.

2. The mixture according to claim 1, characterized in that the weight ratio (i):(ii) is about 13:6.

3. The mixture according to claim 1, characterized in that it comprises (i) protolichesterinic acid or its sodium salt, its potassium salt, its lithium salt, its ammonium salt, or its 4R,5S diastereoisomer or a derivative thereof, and (ii) lichesterinic acid or its sodium salt, its potassium salt, its lithium salt, its ammonium salt, or its 5S enantiomer or a derivative thereof.

4. The mixture according to claim 1, characterized in that it comprises protolichesterinic acid and lichesterinic acid.

5. The mixture according to claim 1, characterized in that it further comprises dihydrolichesterinic acid.

* * * * *